US009963539B2

(12) United States Patent
Zipfel et al.

(10) Patent No.: US 9,963,539 B2
(45) Date of Patent: May 8, 2018

(54) HYDROFLUOROCARBON COMPOSITIONS

(71) Applicant: SOLVAY S.A., Brussels (BE)

(72) Inventors: Lothar Zipfel, Laatzen (DE); Werner Krücke, Hannover (DE); Karsten Börner, Sehnde (DE); Pierre Dournel, Brussels (BE); Dierk-Ingolf Recke, Wunstorf (DE)

(73) Assignee: SOLVAY S.A., Brussels (BE)

( * ) Notice: Subject to any disclaimer, the term of this patent is extended or adjusted under 35 U.S.C. 154(b) by 0 days. days.

(21) Appl. No.: 14/712,175

(22) Filed: May 14, 2015

(65) Prior Publication Data
US 2015/0246997 A1 Sep. 3, 2015

Related U.S. Application Data

(63) Continuation of application No. 12/400,345, filed on Mar. 9, 2009, now abandoned, which is a continuation of application No. 10/548,895, filed as application No. PCT/EP2004/002656 on Mar. 12, 2004, now abandoned.

(60) Provisional application No. 60/465,979, filed on Apr. 28, 2003.

(30) Foreign Application Priority Data

Mar. 13, 2003 (EP) ..................... 03100641

(51) Int. Cl.
C08G 18/76 (2006.01)
C07C 19/08 (2006.01)
C08G 18/18 (2006.01)
C08G 18/32 (2006.01)
C08G 18/40 (2006.01)
C08J 9/14 (2006.01)
C08G 101/00 (2006.01)

(52) U.S. Cl.
CPC .......... *C08G 18/7671* (2013.01); *C07C 19/08* (2013.01); *C08G 18/1816* (2013.01); *C08G 18/3206* (2013.01); *C08G 18/4018* (2013.01); *C08J 9/146* (2013.01); *C08G 2101/005* (2013.01); *C08G 2101/0025* (2013.01); *C08J 2205/052* (2013.01); *C08J 2205/10* (2013.01); *C08J 2375/04* (2013.01)

(58) Field of Classification Search
CPC ........... C08G 18/7671; C08G 18/3206; C08G 18/1816; C08G 18/4018; C08G 2101/005; C08G 2101/0025; C08J 9/146; C08J 2205/10; C08J 2205/052; C08J 2375/04; C07C 19/08
See application file for complete search history.

(56) References Cited

U.S. PATENT DOCUMENTS

| 6,080,799 A | 6/2000 | Kruecke et al. |
| 6,380,275 B1 | 4/2002 | Kruecke et al. |
| 6,451,867 B1 | 9/2002 | Bogdan et al. |
| 6,590,003 B2 | 7/2003 | Eisen et al. |
| 2002/0198274 A1 | 12/2002 | Bogdan et al. |
| 2003/0050351 A1 | 3/2003 | Eisen et al. |

FOREIGN PATENT DOCUMENTS

| DE | 100 28 226 A1 | 12/2001 |
| WO | 02/099006 A1 | 12/2002 |

OTHER PUBLICATIONS

L. Zipfel, et al., "HFC-365mfc and HFC-245fa Progress in Application of New HFC Blowing Agents", Polyurethanes World Congress, 1997, pp. 176-185.

*Primary Examiner* — John Cooney

(57) ABSTRACT

A composition which comprises 1,1,1,3,3-pentafluorobutane-(HFC-365mfc) and 1,1,3,3-pentafluoropropane (HFC-245fa) in a weight ratio HFC-365mfc/HFC-245fa of from 60:40 to 75:25.

7 Claims, No Drawings

HYDROFLUOROCARBON COMPOSITIONS

This application is a continuation of U.S. patent application Ser. No. 12/400,345, filed Mar. 9, 2009, which is a continuation of U.S. patent application Ser. No. 10/548,895, filed Oct. 20, 2005, which is a U.S. national stage entry under 35 U.S.C. § 371 of International Application No. PCT/EP2004/002656, filed Mar. 12, 2004, which claims benefit of U.S. Provisional Application 60/465,979, filed Apr. 28, 2003, and European Application No. EP 03100641.4, filed Mar. 13, 2003. The entire contents of these applications are explicitly incorporated herein by this reference.

The present invention relates to compositions of 1,1,3,3-pentafluorobutane (HFC-365mfc) and 1,1,1,3,3-pertafluoropropane (HFC-245fa), which are useful as blowing agents for polymer foams.

Mixtures HFC-365mfc and HFC-245fa are suitable in particular for the manufacture of polyurethane foams and modified polyurethane foams such as polyisocyanurate foams. U.S. Pat. No. 6,080,799 discloses inter alia a blowing agent mixture of HFC-365mfc/HFC-245fa.

It has been discovered that in certain formulated systems for polyurethanes containing polyols and mixtures of HFC-365mfc and HFC-245fa, a flash point may be observed in spite of the nonflammable nature of the polyols and of the mixtures of HFC-365mfc and HFC-245fa respectively.

It was desirable to find a blowing agent composition which does not display a flash point when used in fully formulated systems and which allows for manufacture of foams which display good insulation properties over a wide temperature range.

Consequently, the invention concerns a composition which comprises 1,1,1,3,3-pentafluorobutane (HFC-365mfc) and 1,1,1,3,3-pentafluoropropane (HFC-245fa) in a weight ratio HFC-365mfc/HFC-245fa of from 60:40 to 75:25.

It has been found, surprisingly, that the compositions according to the invention allow for safe manufacture of (modified) polyurethane foams with fully formulated systems having no flash point whereas obtained closed-cell foams are particularly suitable for thermal insulation at low temperatures, as condensation of the cell gas can be substantially avoided.

Polyurethane is understood to mean the polymers resulting essentially from the reaction of polyols and of isocyanates. These polymers are typically obtained from formulations exhibiting an isocyanate number from 100 to 180. Modified polyurethane is understood to mean the polymers resulting from the reaction of polyols and of isocyanates which contain, in addition to urethane functional groups, other types of functional groups, in particular triisocyanuric rings formed by trimerization of isocyanates. These modified polyurethanes are normally known as polyisocyanurates. These polymers are typically obtained from formulations exhibiting an isocyanate number from 180 to 550.

In the composition according to the invention, the weight ratio HFC-365mfc/HFC-245fa is greater than or equal to 60:40. Often the weight ratio HFC-365mfc/HFC-245fa is greater than or equal to 65:35. Preferably, the weight ratio HFC-365mfc/HFC-245fa is greater than or equal to 67:33. A weight ratio HFC-365mfc/HFC-245fa of about 70:30 is particularly preferred.

In the composition according to the invention, the weight ratio HFC-365mfc/HFC-245fa is lower than or equal to 75:25. Often the weight ratio HFC-365mfc/HFC-245fa is lower than or equal to 73:27. Preferably, the weight ratio HFC-365mfc/HFC-245 fa is lower than or equal to 72:28.

The compositions according to the invention which consist essentially of HFC-365mfc and HFC-245fa are particularly preferred.

The invention concerns also a premix intended for the preparation of polyurethane or modified polyurethane foams comprising
 a) at least one polyol
 b) a catalyst for the reaction of isocyanates with polyols
 c) a composition according to the invention For the purposes of the present invention, premix is understood to mean any composition comprising at least one polyol, at least one blowing agent and at least one catalyst.

Surprisingly, the compositions according to the invention are chemically stable in the premix. Consequently, the latter can optionally be formulated without a stabilizer against the potential degradation of the composition according to the invention.

For the purposes of the present invention, polyol is understood to mean any compound containing at least two functional groups which react with isocyanates. These functional groups contain at least one active hydrogen atom, such as defined by the Zerowittinoff reaction. The active hydrogen atom is generally a hydrogen atom bonded to an oxygen, nitrogen or sulphur atom. Any polyol conventionally used to prepare polyurethane foams can be used in the premixes according to the invention. Mention may in particular be made of polyether polyols and polyester polyols.

The catalyst of the premixes according to the invention comprises a compound with catalyses the formation of the —NH—CO—O— urethane bond by reaction between a polyol and an isocyanate or which activates the reaction between an isocyanate and water, such as tertiary amines and organic tin, iron, mercury or lead compounds. Mention may in particular by made, as tertiary amines, of triethylamine, N,N-dimethylcyclohexylamine (DMCHA), N-methylmorpholine (NMM), N-ethylmorpholine, dimethylethanolamine, diaza[2.2.2]bicyclooctane (triethylenediamine) and substituted benzylamines, such as N,N-dimethylbenzylamine (DB). Mention may in particular be made, as organic tin or lead compounds, of dibutyltin dilaurate, stannous octanoate and lead octanoate.

The catalyst of the premixes according to the invention can, in particular when the latter are intended for the manufacture of modified polyurethane (polyisocyanurate) foams, comprise a compound which catalyses the trimerization of isocyanates to triisocyanurates. Compounds which catalyse the trimerization of isocyanates which can be used in the premixes according to the invention are in particular triazines.

In addition to the polyol, the composition according to the invention and the catalyst, the premixes according to the invention can additionally contain various additives commonly used to prepare polyurethane or modified polyurethane foams, such as, in particular, water, surface-active agents, antioxidizing agents, flame-retardant agents and/or pigments. The more particularly preferred premixes according to the invention are essentially composed of at least one polyol, the composition according to the invention, at least one catalyst which promotes the polyol/isocyanate reaction and at least one of the usual additives mentioned above.

The proportions of polyol catalyst, the composition according to the invention and optional additives in the premixes according to the invention vary, in particular according to the application, the type of foam prepared, the nature of the polyol and the nature of the catalyst.

In practice, the amount of catalyst used generally varies from approximately 0.05 to 10 parts by weight per 100 parts by weight of polyol. In general, the amount of the composition according to the invention is from 1 to 80 parts by weight per 100 parts by weight of polyol. It is preferably from 10 to 60 parts by weight per 100 parts by weight of polyol. The amounts of water, surface-active agents, plasticizing agents end/or flame-retardant agents are those conventionally used to prepare polyurethane or modified polyurethane foams.

The invention also relates to a process for the manufacture of polyurethane or modified polyurethane foams, in which at least one isocyanate is reacted with at least one polyol in the presence of the composition according to the invention, of at least one catalyst and, optionally, of other usual additives.

Any isocyanate conventionally used to manufacture such foams can be used in the process according to the invention. Mention may be made, by way of example, of aliphatic isocyanates, such as hexamethyl one diisocyanate, and aromatic isocyanates, such as tolylene diisocyanate or diphenylmethane diisocyanate.

Generally, the process according to the invention is carried out in the presence of water. In this case the amount of water used is preferably equal to or greater than 1 part by weight per 100 parts of polyol. More preferably, the amount of water used equal to or greater than 1.5 parts by weight per 100 parts of polyol.

In this case the amount of water used is preferably equal to or less than 2.5 parts by weight per 100 parts of polyol. More preferably, the amount of water used equal to or less than 2 parts by weight per 100 parts of polyol.

In the process according to the invention, the composition according to the invention can be supplied to the reaction in the form of the premix according to the invention. The composition according to the invention can also be supplied to the reaction in the form of a mixture of the composition with the isocyanate.

The invention concerns also a polyurethane or modified polyurethane foam which is obtainable according to the process according to the invention. The polyurethane or modified polyurethane foam according to the invention is preferably a rigid closed-cell foam. The polyurethane or modified polyurethane foam can also be selected from a flexible or semi-flexible foam, an integral skin foam and a monocomponent foam.

The invention concerns also a thermal insulation material, which comprises a polyurethane or modified polyurethane foam according to the invention.

Specific examples of thermal insulation material according to the invention include insulation panels, tubes for pipe insulation, sandwich panels, laminates and block foams.

The thermal insulation material according to the invention generally substantially keeps its insulating properties when used in contact with an atmosphere having a temperature of 10° C. or lower. Often the temperature of use can be 5° C. or lower. The temperature can even be 0° C. or lower without substantial condensation. The thermal insulation material according to the invention is particularly suitable when used in contact with an atmosphere having a temperature of −10° C. or higher.

The examples here after are intended to illustrate the invention in a non-limitative manner.

EXAMPLE 1: PUR MANUFACTURE WITH A 70:30 COMPOSITION OF HFC-365MFC AND HFC-245 FA

A preparation of HFC-365mfc/HFC-245fa in a ratio 70:30 starts boiling at 27° C. 100 g Polyol-composition of an aromatic Polyesterpolyol and an aromatic Polyetherolyol with an OH number of 450 and 15 g Tris-Chloroisopropylphosphate as a flame retardant, 2 g Mimethylcyclohexylamine as a catalyst and 15 g of a Siloxanepolyalkene-oxide-Copolymer as a stabilizer, 2 g of water and 20 g of HFC-365mfc/HFC-245fa in a ratio 70:30 were blended and then mixed with 130 g of 4,4-Diisocyanatediphenylmethane. A rigid foam was obtained with a density of 35 kg/m$^3$.

EXAMPLE 2: PUR MANUFACTURE WITH A 75:25 COMPOSITION OF HFC-365MFC/HFC-245FA

Example 1 was repeated with 20 g of HFC-365mfc/HEC-245fa in a ratio 75:25 having a boiling start of 28° C. The density was the same as in Example 2.

EXAMPLE 3

Example 1 was repeated, adding the blowing agent composition separately, at first 14 g HFC-365mfc and then 6 g of HFC-245fa, using a dip tube. A rigid foam was obtained with a density of 35 kg/m$^3$.

The compositions do not present any flash point when used in a premix with polyols.

The invention claimed is:
1. A premix for the preparation of polyurethane or modified polyurethane foams, the premix comprising
   a) at least one polyol,
   b) 0.05 to 10 parts by weight per 100 parts by weight of polyol of a catalyst for the reaction of isocyanates with polyols, wherein the catalyst comprises N,N-dimethylbenzylamine and dibutyltin dilaurate; and
   c) 1 to 80 parts by weight per 100 parts by weight of polyol of a composition consisting of 1,1,1,3,3-pentafluorobutane (HFC-365mfc) and 1,1,1,3,3-pentafluoropropane (HFC-245fa) in a weight ratio HFC-365mfc/HFC-245fa of from 60:40 to 73:27;
   and a flame-retardant agent, said premix being formulated without a stabilizer.

2. The premix according to claim 1, wherein the premix comprises 10 to 60 parts by weight per 100 parts by weight of polyol of the composition consisting of 1,1,1,3,3-pentafluorobutane (HFC-365mfc) and 1,1,1,3,3-pentafluoropropane (HFC-245fa).

3. The premix according to claim 1, wherein the weight ratio HFC-365mfc/HFC-245fa is from 65:35 to 73:27.

4. The premix according to claim 3, wherein the weight ratio HFC-365mfc/HFC-245fa is from 67:33 to 72:28.

5. The premix according to claim 4, wherein the weight ratio HFC-365mfc/HFC-245fa is about 70:30.

6. The premix according to claim 1, wherein the composition consists of 1,1,1,3,3-pentafluorobutane (HFC-365mfc) and 1,1,1,3,3-pentafluoropropane (HFC-245 fa) in a weight ratio HFC-365mfc/HFC-245fa of from 60:40 to 65:35.

7. The premix according to claim 6, wherein the weight ratio HFC-365mfc/HFC-245fa is 60:40.

* * * * *